(12) United States Patent
Park et al.

(10) Patent No.: US 11,952,339 B2
(45) Date of Patent: Apr. 9, 2024

(54) METHOD OF RECOVERING UNREACTED ETHYLENE IN ETHYLENE OLIGOMERIZATION PROCESS

(71) Applicants: SK Innovation Co., Ltd., Seoul (KR); SK Geo Centric Co., Ltd., Seoul (KR)

(72) Inventors: Chansaem Park, Daejeon (KR); Jinhwan Bang, Daejeon (KR); Sungreal Son, Daejeon (KR); Inhyoup Song, Daejeon (KR); Woosung Jung, Daejeon (KR); Eol Han, Daejeon (KR)

(73) Assignees: SK Innovation Co., Ltd., Seoul (KR); SK Geo Centric Co., Ltd., Seoul (KR)

( * ) Notice: Subject to any disclaimer, the term of this patent is extended or adjusted under 35 U.S.C. 154(b) by 65 days.

(21) Appl. No.: 17/629,158

(22) PCT Filed: Jul. 22, 2020

(86) PCT No.: PCT/KR2020/009632
§ 371 (c)(1),
(2) Date: Jan. 21, 2022

(87) PCT Pub. No.: WO2021/015541
PCT Pub. Date: Jan. 28, 2021

(65) Prior Publication Data
US 2022/0267235 A1    Aug. 25, 2022

(30) Foreign Application Priority Data

Jul. 24, 2019   (KR) .................. 10-2019-0089544

(51) Int. Cl.
*C07C 7/04*       (2006.01)
*B01D 3/06*       (2006.01)
(Continued)

(52) U.S. Cl.
CPC .............. *C07C 7/04* (2013.01); *B01D 3/06* (2013.01); *B01D 3/143* (2013.01); *C07C 2/08* (2013.01)

(58) Field of Classification Search
CPC .. C07C 7/04; C07C 2/08; C07C 11/04; B01D 3/06; B01D 3/143; B01J 19/0046; B01J 19/0053; B01J 2219/00452; Y02P 20/582
See application file for complete search history.

(56) References Cited

U.S. PATENT DOCUMENTS

| 5,962,761 A | 10/1999 | Sechrist et al. |
| 2012/0095181 A1 | 4/2012 | Hottovy et al. |

(Continued)

FOREIGN PATENT DOCUMENTS

| CN | 101565348 A | 10/2009 |
| CN | 101874966 A | 11/2010 |

(Continued)

*Primary Examiner* — Ali Z Fadhel
(74) *Attorney, Agent, or Firm* — The Webb Law Firm

(57) ABSTRACT

Provided is a method of recovering unreacted ethylene in an ethylene oligomerization process and reusing the ethylene as a raw material, and more particularly, to a method of recovering unreacted ethylene with an increased recovery rate of reuse. When the method of the present invention is used, most of unreacted ethylene may be dissolved in a solvent to be recovered without loss, and a low boiling point reaction product which is not dissolved in the solvent is removed to prevent an unreacted product from being concentrated in a reactor.

9 Claims, 1 Drawing Sheet

(51) Int. Cl.
*B01D 3/14* (2006.01)
*C07C 2/08* (2006.01)

(56) References Cited

U.S. PATENT DOCUMENTS

| | | |
|---|---|---|
| 2013/0144024 A1 | 6/2013 | Lattner et al. |
| 2015/0126790 A1* | 5/2015 | Venter .................. C07C 2/32 585/511 |
| 2015/0203418 A1 | 7/2015 | Meiswinkel et al. |
| 2016/0325263 A1 | 11/2016 | Uhm et al. |
| 2016/0362350 A1 | 12/2016 | Toda et al. |
| 2017/0198967 A1 | 7/2017 | Jeong et al. |
| 2018/0044266 A1 | 2/2018 | Jeong et al. |
| 2018/0162962 A1 | 6/2018 | Haynie |
| 2018/0237360 A1 | 8/2018 | Han |
| 2018/0354870 A1 | 12/2018 | Wei et al. |
| 2018/0355075 A1 | 12/2018 | Al-Haj Ali et al. |

FOREIGN PATENT DOCUMENTS

| | | |
|---|---|---|
| CN | 107849168 A | 3/2018 |
| JP | 2007153825 A | 6/2007 |
| KR | 101568186 B1 | 11/2015 |
| KR | 1020160125392 A | 10/2016 |
| KR | 1020160144805 A | 12/2016 |
| KR | 1020160144806 A | 12/2016 |
| KR | 101719221 B1 | 3/2017 |
| KR | 1020170028203 A | 3/2017 |
| KR | 1020180082573 A | 7/2018 |
| WO | 2018170054 A1 | 9/2018 |

* cited by examiner

[Fig. 1]
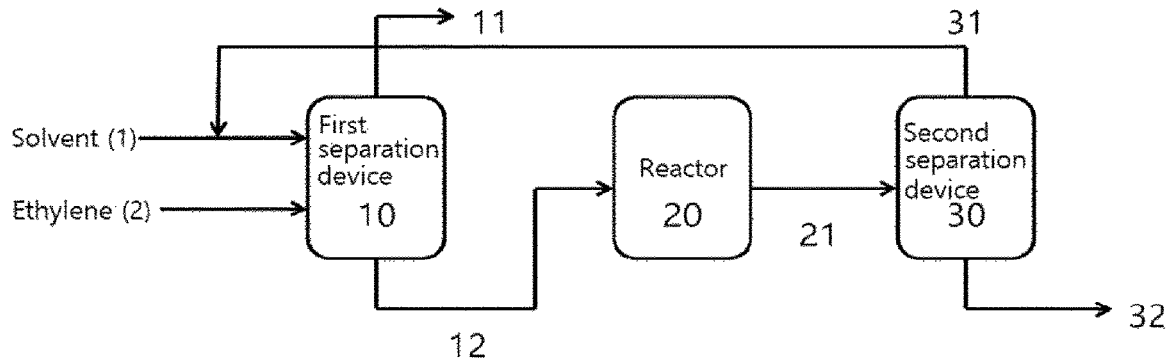
[Fig. 2]
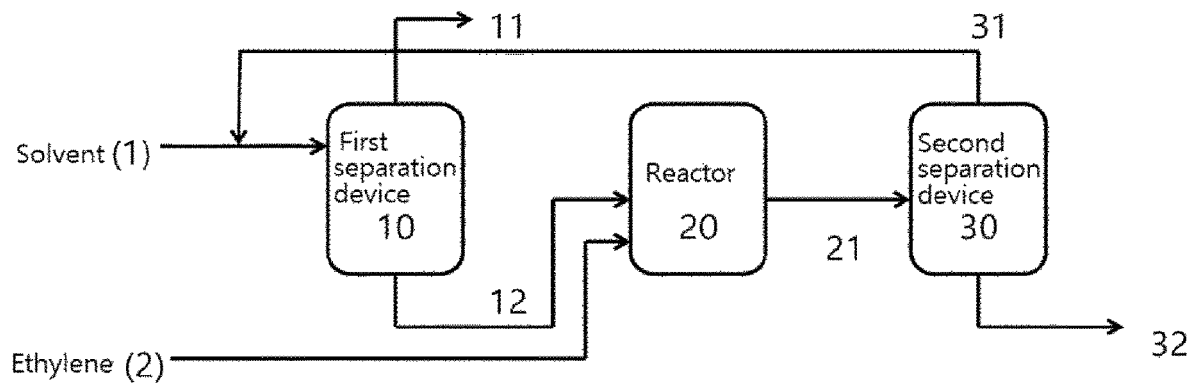
[Fig. 3]
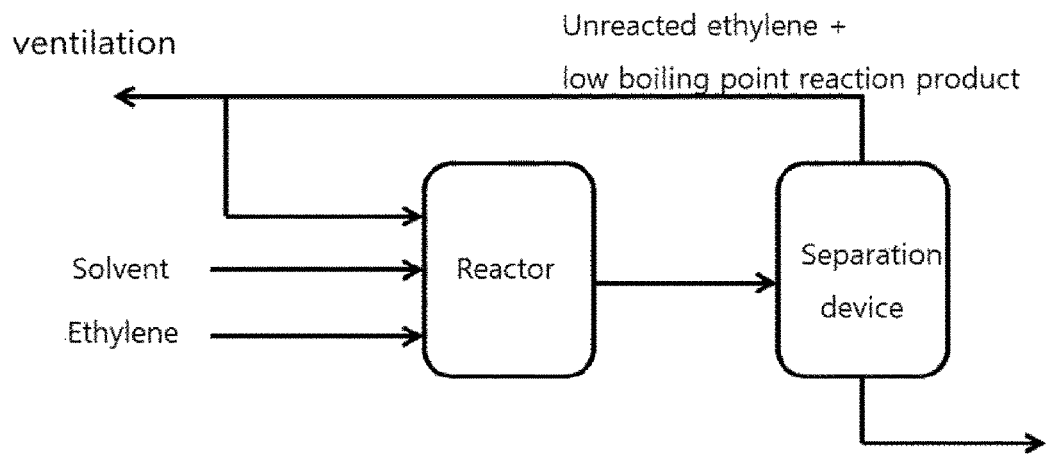

METHOD OF RECOVERING UNREACTED ETHYLENE IN ETHYLENE OLIGOMERIZATION PROCESS

CROSS-REFERENCE TO RELATED APPLICATIONS

This application is the United States national phase of International Application No. PCT/KR2020/009632 filed Jul. 22, 2020, and claims priority to Korean Patent Application No. 10-2019-0089544 filed Jul. 24, 2019, the disclosures of which are hereby incorporated by reference in their entirety.

BACKGROUND OF THE INVENTION

Field of the Invention

The present invention relates to a method of recovering unreacted ethylene in an ethylene oligomerization process and reusing the ethylene as a raw material, and more particularly, to a method of recovering unreacted ethylene with an increased recovery rate of reuse.

Description of Related Art

1-Hexene or 1-octene is an important commercial raw material which is widely used in a polymerization process as a monomer or comonomer for preparing a linear low density polyethylene, and is obtained by purifying a product produced by an oligomerization reaction of ethylene.

A reactor effluent obtained from an ethylene oligomerization reaction includes unreacted ethylene together with 1-hexene and 1-octene, and in order to increase an overall reaction yield, a process of separating the unreacted ethylene from the reactor effluent and returning it to the reactor, is included.

Usually, as shown in FIG. 3, the reactor effluent is transferred to a gas-liquid separation device such as a distillation column and a flash drum and separated, and an upper separated material in the gas-liquid separation device includes unreacted ethylene, methane and ethane which are low boiling point reaction product, and the like, the upper separated material is returned to the reactor. A lower separated material includes a solvent, a linear alpha olefin (LAO) product, and a high-boiling point reaction product, and is transferred to a latter stage separation process.

Here, a part of a recovered stream is ventilated to prevent the low boiling point reaction product included in the recovered stream from being concentrated in the reactor. Since a part of the recovered stream having a high ethylene concentration is ventilated as it is in a usual method, ethylene is largely lost, which hinders economic feasibility of the process.

Therefore, there is needed a method of efficiently recovering the unreacted ethylene.

Korean Patent Laid-Open Publication No. 10-2017-0028203 (Mar. 13, 2017) discloses a configuration in which a reaction effluent is transferred to a gas-liquid separator and separated, and a first gaseous mixture which is an upper separated material of the gas-liquid separator is cooled using a cooler and circulated to an oligomerization reactor, or in the first gaseous mixture, unreacted ethylene and some ethylene oligomer products are separated as a second gaseous mixture including some oligomer adducts and some reaction solvents in a first fractionation column, and the second gaseous mixture is cooled using a cooler and circulated to an oligomerization reactor.

However, when circulation is performed by the above method, since a difference in boiling points between an adduct having a lower boiling point than ethylene and ethylene is not significant, a distillation column having dozens of stages is needed and operation costs are high.

RELATED ART DOCUMENTS

Patent Documents

Korean Patent Laid-Open Publication No. 10-2017-0028203 (Mar. 13, 2017)

SUMMARY OF INVENTION

Technical Problem

An object of the present invention is to provide a method of efficiently recovering unreacted ethylene in an ethylene oligomerization process.

Another object of the present invention is to provide a method of reducing operation costs and investment costs, by allowing separation of unreacted ethylene and a low boiling point reaction product only with distillation having fewer stages of at least one under mild operation conditions.

Solution to Problem

The inventors of the present invention found that since ethylene has a higher solubility in a reaction solvent than ethane and methane which are low boiling point reaction products, only ethylene is dissolved in the reaction solvent using the solubility difference as such and recirculated to a reactor, and it is easy to remove the low boiling point reaction product, thereby completing the present invention.

In one general aspect, a method of recovering unreacted ethylene in an ethylene oligomerization process, includes:
in the ethylene oligomerization process,
mixing a first recovery stream including the unreacted ethylene and a low boiling point reaction product separated in a second separation device in a latter stage of a reactor with a solvent introduced to a reaction raw material, and then transferring the mixture to a first separation device.

Advantageous Effects of Invention

When the method of the present invention is used, most of unreacted ethylene may be dissolved in a solvent to be recovered without loss, and a low boiling point reaction product which is not dissolved in the solvent is removed to prevent an unreacted product from being concentrated in a reactor.

In addition, a recovery stream is transferred in a state of being mixed in advance in a solvent to a separation device, thereby performing phase separation even under relatively mild conditions, and reaction conditions of a separation device are adjusted by making a difference in the composition of the recovery stream and the solubility in the solvent, thereby further improving a recovery rate of unreacted ethylene. In addition, accumulation of the low boiling point reaction product in the reactor may be minimized.

In addition, since only a separation device for phase separation of gas and liquid is added to the conventional method and device in the present invention, there is little increase in operation costs and an economical effect from a decrease in ethylene loss is large.

BRIEF DESCRIPTION OF DRAWINGS

The above and other objects, features and advantages of the present invention will become apparent from the following description of preferred embodiments given in conjunction with the accompanying drawings, in which:

FIG. 1 illustrates an unreacted ethylene recovery process according to an embodiment of the present invention.

FIG. 2 illustrates an unreacted ethylene recovery process according to another embodiment of the present invention.

FIG. 3 illustrates an ethylene oligomerization process of Comparative Example 1.

DETAILED DESCRIPTION OF MAIN ELEMENTS

1: solvent
2: ethylene
10: first separation device
11: first upper effluent
12: first lower effluent
20: reactor
21: first reactant
30: second separation device
31: first recovery stream (second upper effluent)
32: second lower effluent

DESCRIPTION OF THE INVENTION

Hereinafter, the present invention will be described in more detail with reference to specific examples and exemplary embodiments including the accompanying drawings. However, the following specific examples or exemplary embodiments are only a reference for describing the present invention in detail, and the present invention is not limited thereto, and may be implemented in various forms.

In addition, unless otherwise defined, all technical terms and scientific terms have the same meanings as those commonly understood by a person skilled in the art to which the present invention pertains. The terms used herein are only for effectively describing a certain specific example, and are not intended to limit the present invention.

In addition, the singular form used in the specification and claims appended thereto may be intended to also include a plural form, unless otherwise indicated in the context.

An embodiment of the present invention is a method of recovering unreacted ethylene in an ethylene oligomerization process, the method including, in the ethylene oligomerization process:

mixing a first recovery stream including the unreacted ethylene and a low boiling point reaction product separated in a second separation device in a latter stage of a reactor with a solvent introduced to a reaction raw material, and then transferring the mixture to a first separation device.

In an embodiment of the present invention, a first upper effluent including the low boiling point reaction product and a first lower effluent including ethylene and the solvent are separated in the first separation device.

The method of recovering unreacted ethylene in an ethylene oligomerization process according to an embodiment of the present invention may include:

mixing the first recovery stream including the unreacted ethylene and the low boiling point reaction product separated in the second separation device in the latter stage of the reactor with the solvent introduced to the reaction raw material, and then introducing the mixture to a first separation device;

separating the mixture into the first upper effluent including the low boiling point reaction product and the first lower effluent including the ethylene and the solvent in the first separation device;

transferring the first lower effluent in the first separation device to the reactor and performing an ethylene oligomerization reaction; and transferring a first reactant reacted in the reactor to the second separation device, recovering the first recovery stream including the unreacted ethylene and the low boiling point reaction product as a second upper effluent, and separating a reactant including C4 or higher olefin oligomers and the solvent as a second lower effluent.

In an embodiment of the present invention, the ethylene introduced to the reaction raw material may be introduced to the first separation device or the reactor.

In an embodiment of the present invention, the low boiling point reaction product may include any one or more selected from methane, ethane, carbon monoxide (CO), nitrogen ($N_2$), hydrogen ($H_2$), and oxygen ($O_2$).

In an embodiment of the present invention, the first separation device and the second separation device may be any one selected from a flash drum and a distillation column or a combination thereof, respectively.

In an embodiment of the present invention, an oligomerization catalyst introduced to the reaction raw material may be introduced to the first separation device or the reactor.

In an embodiment of the present invention, the solvent introduced to the reaction raw material may be any one selected from toluene, benzene, ethylbenzene, cumene, xylene, hexane, octane, cyclohexane, methyl cyclohexane, diethyl ether, and tetrahydrofuran, or a mixed solvent of two or more thereof.

In an embodiment of the present invention, a content of the solvent introduced to the reaction raw material may satisfy the following Relation 1:

$$0.02 \leq W_e/W_s \leq 1.0 \qquad \text{[Relation 1]}$$

wherein $W_e$ is a content of the unreacted ethylene in the first recovery stream, and $W_s$ is a content of the solvent introduced to the reaction raw material.

In an embodiment of the present invention, operation conditions of the first separation device may be performed under conditions satisfying the following Relations 2 and 3:

$$0.0005 \leq RS_l/(RS_l + W_S) \times 100 \leq 5 \qquad \text{[Relation 2]}$$

$$2 \leq RS_e/(RS_e + W_S) \times 100 \leq 60 \qquad \text{[Relation 3]}$$

wherein $RS_l$ is a content of the low boiling point reaction product dissolved in the solvent in the first separation device, $Rs_e$ is a content of the unreacted ethylene dissolved in the solvent in the first separation device, and $W_s$ is a content of the solvent introduced to the reaction raw material.

In an embodiment of the present invention, operation conditions of the first separation device may be performed under conditions satisfying the following Relations 4 and 5:

$$RS_1/R_1 \times 100 \leq 90 \qquad \text{[Relation 4]}$$

$$95 \leq RS_e/R_e \times 100 \qquad \text{[Relation 5]}$$

wherein $RS_1$ is a content of the low boiling point reaction product dissolved in the solvent in the first separation device and $R_1$ is a content of the low boiling point reaction product in the first recovery stream, and $RS_e$ is a content of the unreacted ethylene dissolved in the solvent in the first separation device and $R_e$ is a content of the unreacted ethylene in the first recovery stream.

In an embodiment of the present invention, operation conditions of the first separation device may be performed under conditions satisfying a relative volatility of the low boiling point reaction product to the unreacted ethylene of 1.5 to 35.0.

Hereinafter, the present invention will be described in detail, referring to the drawings.

An embodiment of the present invention includes mixing a first recovery stream 31 including unreacted ethylene and a low boiling point reaction product separated in a second separation device 30 in a latter stage of a reactor 20 with a solvent 1 introduced to a reaction raw material, and then transferring the mixture to a first separation device 10, as shown in FIG. 1. Here, as shown in FIG. 1, ethylene 2 introduced to the reaction raw material may be transferred to the first separation device 10. In addition, though not shown, an oligomerization catalyst, a cocatalyst, and the like may be transferred to the first separation device 10.

In addition, a first upper effluent 11 including the low boiling point reaction product and a first lower effluent 12 including the ethylene and the solvent may be separated in the first separation device 10.

Specifically, mixing a first recovery stream 31 including unreacted ethylene and a low boiling point reaction product separated in the second separation device 30 in the latter stage of the reactor 20 with the solvent 1 introduced to the reaction raw material, and then introducing the mixture to the first separation device 10;

separating the mixture into the first upper effluent 11 including the low boiling point reaction product and the first lower effluent 12 including the ethylene and the solvent in the first separation device 10;

transferring the first lower effluent 12 in the separation device 10 to the reactor 20 and performing an ethylene oligomerization reaction; and transferring a first reactant 21 reacted in the reactor 20 to the second separation device 30, recovering the first recovery stream 31 including the unreacted ethylene and the low boiling point reaction product as a second upper effluent, and separating a reactant including C4 or higher olefin oligomers and the solvent as a second lower effluent 32, may be included.

More specifically, as shown in FIG. 1, mixing the first recovery stream 31 including the unreacted ethylene and the low boiling point reaction product separated in the second separation device 30 in the latter stage of the reactor 20 with the solvent 1 introduced to the reaction raw material, transferring the mixture to the first separation device 10, and introducing the ethylene 2 introduced to the reaction raw material to the first separation device 10;

separating the mixture into the first upper effluent 11 including the low boiling point reaction product and the first lower effluent 12 including the ethylene and the solvent in the first separation device 10;

transferring the first lower effluent 12 in the separation device 10 to the reactor 20 and performing the ethylene oligomerization reaction; and transferring the first reactant 21 reacted in the reactor 20 to the second separation device 30, recovering the first recovery stream 31 including the unreacted ethylene and the low boiling point reaction product as the second upper effluent, and separating the reactant including C4 or higher olefin oligomers and the solvent as the second lower effluent 32, may be included.

Another embodiment of the present invention includes mixing a first recovery stream 31 including unreacted ethylene and a low boiling point reaction product separated in a second separation device 30 in a latter stage of a reactor 20 with a solvent 1 introduced to a reaction raw material, and then transferring the mixture to a first separation device 10, as shown in FIG. 2. Here, as shown in FIG. 2, ethylene 2 introduced to the reaction raw material may be transferred to the reactor 20. In addition, though not shown, an oligomerization catalyst, a cocatalyst, and the like may be transferred to the reactor 20.

In addition, a first upper effluent 11 including the low boiling point reaction product and a first lower effluent 12 including ethylene and the solvent may be separated in the first separation device 10.

Specifically, mixing the first recovery stream 31 including the unreacted ethylene and the low boiling point reaction product separated in the second separation device 30 in the latter stage of the reactor 20 with the solvent 1 introduced to the reaction raw material, and then introducing the mixture to the first separation device 10;

separating the mixture into the first upper effluent 11 including the low boiling point reaction product and the first lower effluent 12 including the ethylene and the solvent in the first separation device 10;

transferring the first lower effluent 12 in the separation device 10 to the reactor 20 and performing an ethylene oligomerization reaction; and transferring a first reactant 21 reacted in the reactor 20 to the second separation device 30, recovering the first recovery stream 31 including the unreacted ethylene and the low boiling point reaction product as a second upper effluent, and separating a reactant including C4 or higher olefin oligomers and the solvent as a second lower effluent 32, may be included.

More specifically, as shown in FIG. 2, mixing the first recovery stream 31 including the unreacted ethylene and the low boiling point reaction product separated in the second separation device 30 in the latter stage of the reactor 20 with the solvent 1 introduced to the reaction raw material, and then introducing the mixture to the first separation device 10;

separating the mixture into the first upper effluent 11 including the low boiling point reaction product and the first lower effluent 12 including the ethylene and the solvent in the first separation device 10;

transferring the first lower effluent 12 in the separation device 10 and the ethylene 2 introduced to the reaction raw material to the reactor 20 and performing the ethylene oligomerization reaction; and transferring the first reactant 21 reacted in the reactor 20 to the second separation device 30, recovering the first recovery stream 31 including the unreacted ethylene and the low boiling point reaction product as the second upper effluent, and separating the reactant including C4 or higher olefin oligomers and the solvent as the second lower effluent 32, may be included.

Hereinafter, each configuration of the present invention will be described in more detail, based on FIGS. 1 and 2. FIGS. 1 and 2 are only examples for describing the present invention in more detail, and the present invention is not limited thereto.

As shown in FIGS. 1 and 2, a first recovery stream includes unreacted ethylene and a low boiling point reaction product, and conventionally, these were ventilated and the low boiling point reaction product included in a recovered stream was prevented from being concentrated in the reactor. The inventors of the present invention studied for preventing the low boiling point reaction product from being concentrated in the reactor, while reusing the unreacted ethylene included in the recovered stream as a raw material. As a result, the inventors found that as shown in FIGS. 1 and 2, the first recovery stream is mixed with a solvent introduced to a reaction raw material, thereby dissolving the unreacted ethylene having a high solubility in the solvent and separating and removing the low boiling point reaction product having a relatively low solubility by the first separation device. In addition, the inventors found that by controlling the reaction conditions of the first separation device depending on the composition of the first recovery stream, the unreacted ethylene is mixed well with the solvent and transferred to the reactor, and by ventilating and removing the low boiling point reaction product, the low boiling point reaction product is prevented from being concentrated in the reactor.

In an embodiment of the present invention, the final product to be produced by the ethylene oligomerization process is an ethylene trimer and an ethylene tetramer, and more specifically 1-hexene and 1-octene.

In an embodiment of the present invention, a solvent and ethylene are introduced to a reaction raw material, and also, an oligomerization catalyst, a cocatalyst, and the like which are commonly used in the art may be further introduced. Here, ethylene, the oligomerization catalyst, and the cocatalyst introduced to the reaction raw material may be introduced to the first separation device 10 or the reactor 20. Otherwise, they may be divided and introduced to the first recovery stream 10 and the reactor 20.

"Introduced to a reaction raw material" in the present invention means a raw material being not recovered from the first reaction raw material but newly introduced.

The solvent 1 is mixed with the first recovery stream 31 and transferred to the first separation device 10, as described above. Here, the mixing may be mixing in a tube to which the solvent is introduced using a line mixer. Otherwise, mixing may be performed in an agitator in the first separation device or in a device by installing an ethylene sparger.

When the first recovery stream 31 is mixed with the solvent in advance and introduced, as described above, separation efficiency may be further improved by using a solubility difference between the unreacted ethylene and the low boiling point reaction product, the number of stages of the first separation device 11 may be reduced, and the reaction may be performed under mild conditions.

When the first recovery stream 31 is not mixed with the solvent and directly transferred to the first separation device 10, a gas separator should be used for separating the unreacted ethylene and the low boiling point reaction product, and cryogenic distillation should be operated at a very low temperature of about −90° C. or lower, and thus, operation costs for maintaining the temperature is high. In addition, pressure swing adsorption has high investment cost consumption for continuous operation.

The first recovery stream 31 is separated as the upper effluent in the second separation device 30, and includes unreacted ethylene and a low boiling point reaction product.

The unreacted ethylene means ethylene remaining without participating the reaction, after an ethylene oligomerization reaction in the reactor, of ethylene introduced to the reaction raw material.

The low boiling point reaction product may include any one or two or more selected from methane, ethane, carbon monoxide (CO), nitrogen ($N_2$), hydrogen ($H_2$), and oxygen ($O_2$).

The solvent 1 introduced to the reaction raw material may be used without limitation as long as it may dissolve ethylene, and more preferably, a solvent having a high solubility in ethylene and a lower solubility in the low boiling point reaction product than ethylene is used. Specifically, for example, the solvent may be any one selected from toluene, benzene, ethylbenzene, cumene, xylene, hexane, octane, cyclohexane, methyl cyclohexane, diethyl ether, tetrahydrofuran, and the like, or a mixed solvent of two or more thereof.

A content of the solvent introduced to the reaction raw material may satisfy the following Relation 1:

$$0.02 \le W_e/W_s \le 1.0 \qquad \text{[Relation 1]}$$

wherein $W_e$ is a content of the unreacted ethylene in the first recovery stream, and $W_s$ is a content of a solvent introduced to a reaction raw material.

Within the range satisfying the above Relation 1, more preferably in a range of $0.05 \le W_e/W_s \le 0.8$, most of ethylene in the first recovery stream is dissolved in the solvent introduced, and the low boiling point reaction product is separated as a gas phase without being dissolved in the solvent, and thus, ethylene and the low boiling point reaction product may be effectively separated.

In an embodiment of the present invention, the first separation device 10 is provided in a former stage of the reactor 20, to which a solvent and ethylene which are raw materials and a recovered first recovery stream are introduced, and the first separation device serves to separate a first upper effluent 11 including a low boiling point reaction product and a first lower effluent 12 including ethylene and the solvent. The first separation device 10 may be any one selected from a flash drum and a distillation column or a combination thereof. Otherwise, the first separation device may be composed of one or more stages, specifically one stage or a plurality of stages of two or more. More specifically, the first separation device may be composed of one stage, and the unreacted ethylene and the low boiling point reaction product may be separated only with one stage.

The operation conditions of the first separation device 10 may be changed depending on the contents of the unreacted ethylene and the low boiling point reaction product present in the recovered first recovery stream 31 and the type of the solvent to be introduced to the reaction raw material. Specifically, it is preferred that the first separation device is operated so that the unreacted ethylene is better dissolved in the solvent and the low boiling point reaction product is less dissolved in the solvent to be removed.

More specifically, for example, the first separation device may be operated under conditions satisfying the following Relations 2 and 3:

$$0.0005 \leq RS_1/(RS_1 + W_S) \times 100 \leq 5 \quad \text{[Relation 2]}$$

$$2 \leq RS_e/(RS_e + W_S) \times 100 \leq 60 \quad \text{[Relation 3]}$$

wherein $RS_1$ is a content of the low boiling point reaction product dissolved in the solvent in the first separation device, $Rs_e$ is a content of the unreacted ethylene dissolved in the solvent in the first separation device, and $W_s$ is a content of the solvent introduced to the reaction raw material.

In the range satisfying the above Relations 2 and 3, more preferably in the range of $0.0005 \leq RS_1/(RS_1+W_s) \times 100 \leq 3$, $2 \leq RS_e/(RS_e+W_s) \times 100 \leq 40$, a difference between the solubility of the low boiling point reaction product in the solvent and the solubility of ethylene in the solvent is large, and the low boiling point reaction product may be removed with decreased loss of ethylene, which is thus preferred.

In addition, the operation conditions of the first separation device may be performed under conditions satisfying the following Relations 4 and 5:

$$RS_1/R_1 \times 100 \leq 90 \quad \text{[Relation 4]}$$

$$95 \leq RS_e/R_e \times 100 \quad \text{[Relation 5]}$$

wherein $RS_1$ is a content of the low boiling point reaction product dissolved in the solvent in the first separation device and $R_1$ is a content of the low boiling point reaction product in the first recovery stream, and $RS_e$ is a content of the unreacted ethylene dissolved in the solvent in the first separation device and $R_e$ is a content of the unreacted ethylene in the first recovery stream.

In the range satisfying the above Relations 4 and 5, a difference between the recovery rate of the low boiling point reaction product in the solvent and the recovery rate of ethylene in the solvent is large, and the low boiling point reaction product may be removed with decreased loss of ethylene, which is thus preferred.

In addition, operation conditions of the first separation device may be performed under conditions satisfying a relative volatility of the low boiling point reaction product to the unreacted ethylene of 1.5 to 35.0. The relative volatility is calculated by the following Equation 1:

$$\text{Relative volatility} = (y_i/x_i)(y_j/x_j) = K_i/K_j \quad \text{[Equation 1]}$$

wherein $K_i$ is a volatility of component i (unreacted ethylene) and $K_j$ is a volatility of component j (low boiling point reaction product). $y_i$ means a concentration of component i in a gas phase, and $x_i$ means a concentration of component i in a liquid phase, in the case in which gas-liquid phase separation occurs in a binary system. $y_j$ means a concentration of component j in a gas phase, and $x_j$ means a concentration of component j in a liquid phase, in the case in which gas-liquid phase separation occurs in a binary system.

Under the condition that the relative volatility of 1.5 to 35.0, more specifically 2.0 to 20.0, is satisfied, it becomes easy to separate the low boiling point reaction product and ethylene by the solvent, and thus, separation by distillation of a small number of stages of at least one is possible and the low boiling point reaction product may be effectively removed with minimized loss of ethylene, which is thus preferred.

Under the conditions satisfying all of Relations 1 to 5, the recovery rate of the low boiling point reaction product may satisfy 90% or less, and the recovery rate of the unreacted ethylene may satisfy 95% or more.

The recovery rate of the low boiling point reaction product is calculated by the following Equation 2:

$$\begin{aligned}\text{Recovery rate (\%) of low boiling point reaction product} = \\ \text{(amount of low boiling point reaction product} \\ \text{dissolved in solvent/amount of low boiling} \\ \text{point reaction product recovered)} \times 100\end{aligned} \quad \text{[Equation 2]}$$

In the above Equation 2, "recovered" may refer to recovered by the first recovery stream, and the recovered amount may be measured by a flowmeter. In addition, the "amount of low boiling point reaction product recovered" means the amount of the low boiling point reaction product in the first recovery stream.

The recovery rate of the unreacted ethylene is calculated by the following Equation 3:

$$\begin{aligned}\text{Recovery rate (\%) of unreacted ethylene} = \\ \text{(amount of unreacted ethylene dissolved in solvent/} \\ \text{amount of recovered unreacted ethylene)} \times 100\end{aligned} \quad \text{[Equation 3]}$$

In the above Equation 3, "recovered" may refer to recovered by the first recovery stream, and the recovered amount may be measured by a flowmeter. In addition, the "amount of recovered unreacted ethylene" means the amount of the unreacted ethylene in the first recovery stream.

The amount of the low boiling point reaction product accumulated in the process of the reactor is determined by the recovery rate of the low boiling point reaction product. The recovery rate of the low boiling point reaction product of 100% means that the low boiling point reaction product is not removed in the first separation device at all, and all accumulated in the reactor. When the recovery rate of the low boiling point reaction product is 99%, the concentration of the low boiling point reaction product in the reactor is concentrated up to 100 times, when the recovery rate of the low boiling point reaction product is 95%, the concentration of the low boiling point reaction product is concentrated up to 20 times, and when the recovery rate of the low boiling point reaction product is 90%, the concentration of the low boiling point reaction product is concentrated up to 10 times the concentration of the produced low boiling point reaction product. As the concentrated amount is increased, a reactor volume is increased and a flow rate of the recovery stream is increased. This causes operation costs of a compressor and investment costs to increase. Therefore, the lower the recovery rate of the low boiling point reaction product, the better, but when the recovery rate of the low boiling point reaction product is lowered, the recovery rate of the unreacted ethylene tends to be lowered, and thus, it is preferred that recovery rate of the low boiling point reaction product is 90% or less. When the recovery rate of the unreacted ethylene is decreased, loss of the unreacted ethylene is relatively increased, and thus, it is preferred that the process is performed in a range of the recovery rate of the low boiling point reaction product of 90% or less, and more specifically 20 to 90%.

In the range of satisfying the range, the recovery rate of the unreacted ethylene may satisfy 95% or more.

More specifically, for example, when the solvent is methyl cyclohexane, the content of the unreacted ethylene in the first recovery stream is 90 to 99 wt %, and the first recovery stream is mixed with the solvent in the range of the content of the unreacted ethylene to the solvent of 2 to 100 wt % and injected to the first separation device, the operation condition of the first separation device may be operation at a temperature of −20 to 50° C. and a pressure of 10 to 60 bar. Within the range, the solubility of the unreacted ethylene in the solvent is higher than that of the low boiling point reaction product and a large amount of the unreacted ethylene may be dissolved in the solvent, which is thus preferred.

In an embodiment of the present invention, the reactor 20 is not limited as long as it is a common reactor used in the ethylene oligomerization process. In addition, the operation conditions are not limited as long as they are common conditions.

More specifically, for example, the first lower effluent 12 separated in the first separation device 10 flows into the reactor 20 and the ethylene oligomerization reaction may be performed. Here, if necessary, ethylene, the oligomerization catalyst, and the like introduced to the reaction raw material may be introduced to the reactor 20. The operation conditions may be performed at a temperature of 40 to 100° C. and a pressure of 10 to 100 bar.

The ethylene oligomerization reaction is performed in the reactor 20, and a first reactant 21 in which a reaction product such as 1-hexene and 1-octene, unreacted ethylene, a low boiling point reaction product, and the like are mixed flows out.

In an embodiment of the present invention, the second separation device 30 is provided in the latter stage of the reactor 20, and the first reactant 21 flowing out from the reactor 20 flows into the second separation device and separated into a second upper effluent 31 and a second lower effluent 32.

The second upper effluent 31 means a first recovery stream including unreacted ethylene and a low boiling point reaction product. The low boiling point reaction product means a component except the unreacted ethylene and specifically, for example, may include any one or more selected from methane, ethane, carbon monoxide (CO), nitrogen ($N_2$), hydrogen ($H_2$), and oxygen ($O_2$).

The second lower effluent 32 includes a reactant including a C4 or higher olefin oligomer such as 1-hexene and 1-octene and a solvent.

The second separation device 30 may be any one selected from a flash drum and a distillation column or a combination thereof. Otherwise, the second separation device may be composed of one or more stages, specifically one stage or a plurality of stages of two or more. The operation conditions of the second separation device 30 are not limited, but may be performed at a temperature of −20 to 50° C. and a pressure of 5 to 95 bar.

In an embodiment of the present invention, in addition to the first separation device 10, the reactor 20, and the second separation device 30, other devices and process which are commonly used in the art may be further included, and any further description therefor will be omitted.

Hereinafter, the present invention will be described in more detail with reference to the Examples and Comparative Examples. However, the following Examples and Comparative Examples are only an example for describing the present invention in detail, and do not limit the present invention in any way.

EXAMPLE 1

The pressure and the temperature were adjusted as shown in the following Table 1, and simulation was performed using Aspen plus V8.6 (AspenTech).

An ethylene oligomerization reaction unit including an ethylene recovery process was designed as shown in FIG. 2. The reactant flowing out from an ethylene oligomerization reactor under the conditions of 60° C. and 60 bar included 9 wt % of unreacted ethylene, 1 wt % of methane, 22 wt % of C4 or higher olefins, 68 wt % of methyl cyclohexane.

The reactant was transferred to a heat exchanger and cooled to 5° C., and the cooled reactant was transferred to a distillation column which is a second separation device where a first recovery stream including unreacted ethylene and methane flowed out in an upper portion, and methyl cyclohexane and C4 or higher olefins were separated in a lower portion. Here, the pressure of the distillation column was 20 bar and the upper temperature was −20° C. The upper separated material included 90 wt % of ethylene and 10 wt % of methane, mixed with methyl cyclohexane having a flow rate of 7.1 times the content of the unreacted ethylene recovered through a recovery line, and transferred to a flash drum which is the first separation device and flashed.

Here, the flash drum was cooled to −20° C. by a refrigerant and the pressure was maintained at 15 bar. Under the flash drum operation conditions, a methane solubility was 1.23 wt % and a unreacted ethylene solubility was 13.25 wt % and thus, a larger amount of ethylene than methane may be dissolved in the solvent, and the relative volatility was 5.6, and it may be confirmed that methane and ethylene was easily separated using the flash drum.

In addition, the recovery rate of methane of the first lower effluent separated from the flash drum was 80.1 wt %, and the recovery rate of the unreacted ethylene thereof was 95.7 wt %, and it may be confirmed that ethylene loss was small.

When the first upper effluent of the flash drum was ventilated, ethylene loss was 1.8 wt % of ethylene introduced to the reaction raw material (feed ethylene), and the first upper effluent was 34 wt % of methane and 66 wt % of ethylene, and thus, a methane concentration therein was higher than that in the recovery line. The first lower effluent was transferred to the reactor, and the feed ethylene, a catalyst, and a cocatalyst were introduced together to the reactor, where an ethylene oligomerization reaction occurred.

EXAMPLES 2 AND 3

As shown in the following Table 1, the ethylene oligomerization reaction was performed in the same manner as in Example 1, except that the operation conditions of the first separation device were changed depending on the composition of the first recovery stream. The results are shown in the following Table 2.

TABLE 1

|  |  |  | Example 1 | Example 2 | Example 3 |
|---|---|---|---|---|---|
| First separation device | Pressure | bar | 15 | 10 | 20 |
|  | Temperature | °C | −20 | 45 | 25 |
| Content of unreacted ethylene with respect to solvent($W_e/W_s$) × 100 |  | wt % | 14 | 4 | 6 |
| Recovery stream composition | Methane | wt % | 10 | 5 | — |
|  | Carbon oxide | wt % | — | — | 4 |
|  | Ethylene | wt % | 90 | 95 | 96 |

TABLE 2

|  |  | Example 1 | Example 2 | Example 3 |
|---|---|---|---|---|
| Solubility of low boiling point reaction product($RS_1/(RS_1 + W_S)$) × 100 | wt % | 1.23 | 0.17 | 0.34 |
| Solubility of unreacted ethylene($RS_e/(RS_e + W_S)$) × 100 | wt % | 13.25 | 3.53 | 9.46 |
| Recovery rate of low boiling point reaction product($RS_1/R_1$ × 100) | wt % | 80.1 | 88.8 | 85.9 |
| Recovery rate of unreacted ethylene($RS_e/R_e$ × 100) | wt % | 95.72 | 96.5 | 98.5 |
| Relative volatility | — | — | 5.6 | 3.4 | 10.9 |

COMPARATIVE EXAMPLE 1

The ethylene oligomerization process was designed as shown in FIG. 3, and the conditions of the reactor and the second separation device in the latter stage were the same as Example 1. In order to obtain the same composition of the recovery stream as Example 1 (90 wt % of ethylene and 10 wt % of methane), 20% of the recovery stream should be ventilated, and thus, 7.5 wt % of loss of the feed ethylene occurred.

Thus, it was confirmed that a large amount of ethylene loss may be decreased by the recovery process of the present invention.

COMPARATIVE EXAMPLE 2

The process was designed under the same conditions as Comparative Example 1, and in order to obtain the same ethylene loss (1.8 wt % of feed ethylene) as the Example, a ventilation rate of the recovery stream should be lowered to 5%, which resulted in an increase of a methane amount accumulated in the process of 4 times, and the composition of the recovery stream was 31 wt % of methane and 69 wt % of ethylene.

As a result, a recovery stream flow rate was increased to increase recycle compressor operation costs and investment costs. The recycle compressor means a compressor which is used for pressurization for sending the first recovery stream to the reactor again.

The invention claimed is:

1. A method of recovering unreacted ethylene in an ethylene oligomerization process, the method comprising:
in the ethylene oligomerization process,
mixing a first recovery stream comprising the unreacted ethylene and a low boiling point reaction product separated in a second separation device in a latter stage of a reactor with a solvent introduced to a reaction raw material;
transferring the mixture to a first separation device, wherein an oligomerization catalyst introduced to a reaction raw material is introduced to the first separation device;
separating the mixture into a first upper effluent comprising the low boiling point reaction product and a first lower effluent comprising the ethylene and the solvent in the first separation device;
transferring the first lower effluent in the first separation device to the reactor and performing an ethylene oligomerization reaction; and
transferring a first reactant reacted in the reactor to the second separation device and recovering the first recovery stream comprising the unreacted ethylene and the low boiling point reaction product as a second upper effluent and separating a reactant comprising C4 or higher olefin oligomers and the solvent as a second lower effluent.

2. The method of recovering unreacted ethylene of claim 1, wherein the ethylene introduced to a reaction raw material is introduced to the first separation device or the reactor.

3. The method of recovering unreacted ethylene of claim 1, wherein the low boiling point reaction product comprises any one or more selected from methane, ethane, carbon monoxide (CO), nitrogen ($N_2$), hydrogen ($H_2$), and oxygen ($O_2$).

4. The method of recovering unreacted ethylene of claim 1, wherein the first separation device and the second separation device are any one selected from a flash drum and a distillation column or a combination thereof, respectively.

5. The method of recovering unreacted ethylene of claim 1, wherein the solvent introduced to a reaction raw material is any one selected from toluene, benzene, ethylbenzene, cumene, xylene, hexane, octane, cyclohexane, methyl cyclohexane, diethyl ether, and tetrahydrofuran, or a mixed solvent of two or more thereof.

6. The method of recovering unreacted ethylene of claim 1, wherein a content of the solvent introduced to a reaction raw material satisfies the following Relation 1:

$$0.02 \leq W_e/W_s \leq 1.0 \quad [\text{Relation 1}]$$

wherein $W_e$ is a content of unreacted ethylene in the first recovery stream, and $W_s$ is a content of the solvent introduced to a reaction raw material.

7. The method of recovering unreacted ethylene of claim 1, wherein operation conditions of the first separation device are performed under conditions satisfying the following Relations 2 and 3:

$$0.0005 \leq RS_1/(RS_1 + W_S) \times 100 \leq 5 \quad [\text{Relation 2}]$$

$$2 \leq RS_e/(RS_e + W_S) \times 100 \leq 60 \quad [\text{Relation 3}]$$

wherein $RS_1$ is a content of the low boiling point reaction product dissolved in the solvent in the first separation device, $Rs_e$ is a content of the unreacted ethylene dissolved in the solvent in the first separation device, and $W_s$ is a content of the solvent introduced to the reaction raw material.

8. The method of recovering unreacted ethylene of claim 7, wherein the operation conditions of the first separation device are performed under conditions satisfying the following Relations 4 and 5:

$$RS_1/R_1 \times 100 \leq 90 \quad \text{[Relation 4]}$$

$$95 \leq RS_e/R_e \times 100 \quad \text{[Relation 5]}$$

wherein $RS_1$ is a content of the low boiling point reaction product dissolved in the solvent in the first separation device and $R_1$ is a content of the low boiling point reaction product in the first recovery stream, and
$RS_e$ is a content of the unreacted ethylene dissolved in the solvent in the first separation device and $R_e$ is a content of the unreacted ethylene in the first recovery stream.

9. The method of recovering unreacted ethylene of claim 1, wherein the operation conditions of the first separation device are performed under conditions satisfying a relative volatility of the low boiling point reaction product to the unreacted ethylene of 1.5 to 35.0.

\* \* \* \* \*